US008822428B2

(12) United States Patent
Collin-Djangone et al.

(10) Patent No.: US 8,822,428 B2
(45) Date of Patent: *Sep. 2, 2014

(54) DOUBLE-STRANDED RNA OLIGONUCLEOTIDES WHICH INHIBIT TYROSINASE EXPRESSION

(71) Applicant: L'Oreal, Paris (FR)

(72) Inventors: Christine Collin-Djangone, Amblainville (FR); Jean-Thierry Simmonet, Cachan (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/792,443

(22) Filed: Mar. 11, 2013

(65) Prior Publication Data

US 2013/0195966 A1 Aug. 1, 2013

Related U.S. Application Data

(60) Division of application No. 12/252,125, filed on Oct. 15, 2008, now Pat. No. 8,410,260, which is a continuation of application No. 11/524,315, filed on Sep. 21, 2006, now abandoned.

(30) Foreign Application Priority Data

Sep. 21, 2005 (FR) .................................... 05 09658

(51) Int. Cl.
C12N 15/11 (2006.01)
C07H 21/02 (2006.01)
A61K 9/127 (2006.01)

(52) U.S. Cl.
USPC .......................... 514/44 A; 536/24.5; 424/450

(58) Field of Classification Search
None
See application file for complete search history.

(56) References Cited

U.S. PATENT DOCUMENTS

| | | | |
|---|---|---|---|
| 6,087,341 | A | 7/2000 | Khavari et al. |
| 7,056,704 | B2 | 6/2006 | Tuschl et al. |
| 7,087,743 | B2 | 8/2006 | Kurfurst et al. |
| 8,410,260 | B2 * | 4/2013 | Collin-Djangone et al. 536/24.5 |
| 2002/0064876 | A1 | 5/2002 | Yoon |
| 2003/0104410 | A1 | 6/2003 | Mittmann |
| 2004/0215006 | A1 | 10/2004 | Bennett et al. |
| 2005/0130181 | A1 | 6/2005 | McSwiggen |
| 2005/0137151 | A1 | 6/2005 | Binetti et al. |
| 2005/0181382 | A1 | 8/2005 | Zamort et al. |
| 2005/0222071 | A1 | 10/2005 | Duranton et al. |
| 2005/0266410 | A1 | 12/2005 | Walsh et al. |
| 2005/0266414 | A1 | 12/2005 | Lyons et al. |
| 2006/0134221 | A1 | 6/2006 | Geall |

FOREIGN PATENT DOCUMENTS

| | | |
|---|---|---|
| CA | 2 136 705 A1 | 5/1995 |
| CN | 1293038 A1 | 5/2001 |
| CN | 1500808 A1 | 6/2004 |
| CN | 1600858 A | 3/2005 |
| EP | 1 564 286 A1 | 8/2005 |
| FR | 2 804 960 A1 | 8/2001 |
| FR | 2 840 217 A1 | 12/2003 |
| FR | 2 864 540 A1 | 7/2005 |
| JP | 08 140699 A1 | 6/1996 |
| JP | 2003/284553 A1 | 10/2003 |
| WO | 95/34680 A1 | 12/1995 |
| WO | 98/10095 A1 | 3/1998 |
| WO | 00/18926 A1 | 4/2000 |
| WO | 00/20460 A1 | 4/2000 |
| WO | 01/40475 A2 | 6/2001 |
| WO | 02/38755 A1 | 5/2002 |
| WO | 02/070751 A1 | 9/2002 |
| WO | 02/072882 A2 | 9/2002 |
| WO | 03/022307 A1 | 3/2003 |
| WO | 03/040325 A2 | 5/2003 |
| WO | 03/057146 A2 | 7/2003 |
| WO | 03/059384 A1 | 7/2003 |
| WO | 03/087331 A2 | 10/2003 |
| WO | WO 03/101376 | 12/2003 |
| WO | 2004/044163 A2 | 5/2004 |
| WO | 2005/042031 A2 | 5/2005 |
| WO | 2005/059125 A1 | 6/2005 |
| WO | 2005/060536 A2 | 7/2005 |
| WO | 2005/118810 A1 | 12/2005 |
| WO | 2006/002433 A2 | 1/2006 |
| WO | 2006/013610 A1 | 2/2006 |
| WO | 2006/014477 A1 | 2/2006 |
| WO | 2006/065067 A2 | 6/2006 |

OTHER PUBLICATIONS

Aimee L. Jackson et al. *Expression profiling reveals off-target gene regulation by RNAi*, Nature Biotechnology 1-3 (2003).
Aimee L. Jackson et al. *Widespread siRNA "off-target" transcript silencing mediated by seed region sequence complementarity*, 12 RNA 1179-1187 (2006).
Kim et al., *Synthetic dsRNA Dicer substrates enhance RNAi potency and efficacy*, Nature Biotechnology, vol. 23, No. 2, pp. 222-226, Feb. 2005.
Keilholz et al., *Quantitative Detection of Circulating Tumor Cells in Cutaneous and Ocular Melanoma and Quality Assessment by Real-Time Reverse Transcriptase-Polymerase Chain Reaction*, Clinical Cancer Research, vol. 10, pp. 1605-1612, Mar. 2004.
European Search Report issued for EP 06 29 1443 on Mar. 8, 2007, 12 pages.

(Continued)

Primary Examiner — Richard Schnizer
(74) Attorney, Agent, or Firm — Buchanan Ingersoll & Rooney PC

(57) ABSTRACT

Novel double-stranded RNA oligonucleotides are useful for decreasing tyrosinase expression, have cosmetic and/or pharmaceutical applications, for example are useful skin depigmenting or anti-browning agents, and can be associated with cationic particles less than or equal to 1 μm in size, having a zeta potential of from 10 to 80 mV.

5 Claims, No Drawings

(56) References Cited

OTHER PUBLICATIONS

Angela Reynolds et al., *Induction of the interferon response by siRNA is cell type- and duplex length-dependent*, 12 RNA 988-993 (2006).

Chaya Chintamaneni et al., *A single base insertion in the putative transmembrane domain of the tyrosinase gene as a cause for tyrosinase-negative oculocutaneous albinism*, 88 Proc. Natl. Acad. Sci 5272-5276 (Jun. 1991).

Tushchl et al., *Selection of siRNA duplexes from the target mRNA sequence*, The siRNA User Guide, 6 Pages, (2003).

Decision of Rejection mailed on Mar. 12, 2013, in corresponding Japanese Patent Application 2006-254695.

* cited by examiner

DOUBLE-STRANDED RNA OLIGONUCLEOTIDES WHICH INHIBIT TYROSINASE EXPRESSION

CROSS-REFERENCE TO RELATED APPLICATIONS

This application is a divisional Application of U.S. patent application Ser. No. 12/252,125, filed on Oct. 15, 2008, which is a continuation of U.S. patent application Ser. No. 11/524,315 filed on Sep. 21, 2006, now abandoned, which claims priority under 35 U.S.C. §119 of FR 05/09658, filed on Sep. 21, 2005, which are hereby expressly incorporated by reference and assigned to the assignee hereof.

BACKGROUND OF THE INVENTION

1. Technical Field of the Invention

The present invention relates to novel double-stranded RNA oligonucleotides for decreasing tyrosinase expression, to the use thereof for cosmetic and/or pharmaceutical purposes and also to the association thereof with cationic particles less than or equal to 1 µm in size, with a zeta potential ranging from 10 to 80 mV.

2. Description of Background and/or Related and/or Prior Art

Tyrosinase (monophenol dihydroxyl phenylalanine: oxygen oxidoreductase EC 1.14.18.1) is the essential enzyme involved in the mechanism of skin pigmentation. It catalyzes in particular the reaction for conversion of tyrosine to Dopa (dihydroxyphenylalanine) by virtue of its hydroxylase activity and the reaction for conversion of Dopa to dopaquinone by virtue of its oxidase activity. The tyrosinase acts only when it is in the maturation state under the action of certain biological factors.

This enzyme can also be advantageous in the treatment of pathologies such as melanoma (Riley et al., J. Immunother., 2001, 21, 212-220) or Vogt-Koyanagi-Harada disease (Read et al., Curr. Opin. Ophthalmol., 2000, 11, 437-442).

The mechanism of formation of skin pigmentation, i.e., the formation of melanin, is particularly complex and involves schematically the following main steps:

Tyrosine Dopa→Dopaquinone→Dopachrome→Melanin

Thus, the pigmentation of human skin results from the synthesis of melanin by dendritic cells, melanocytes. The latter contain organelles called melanosomes, which are the site of melanin biosynthesis. It is the melanosomes which, after migration along the dendrites, are transferred from the melanocytes to the keratinocytes. The keratinocytes are then transported to the surface of the skin during the epidermal differentiation process (Gilchrest B A, Park H Y, Eller M S, Yaar M, Mechanisms of ultraviolet light-induced pigmentation, Photochem Photobiol., 1996; 63: 1-10; Hearing V J, Tsukamodo K, Enzymatic control of pigmentation in mammals, FASEB J., 1991; 5: 2902-2909).

Among melanogenesis enzymes, tyrosinase is a key enzyme which catalyses the first two steps of melanin synthesis. Homozygous mutations for tyrosinase cause oculocutaneous albinism type I characterized by a complete absence of melanin synthesis (Toyofuku K, Wada I, Spritz R A, Hearing V J, The molecular basis of oculocutaneous albinism type 1 (OCA1): sorting failure and degradation of mutant tyrosinases results in a lack of pigmentation, Biochem J., 2001; 355: 259-269).

Since hyperpigmentation disorders result from an increase in melanin production, the development of novel therapeutic approaches, the rationale of which is based on the inhibition of tyrosinase activity, is found to be important.

Most of the skin-lightening compounds already known are phenols/catechols. These compounds inhibit tyrosinase but most of these compounds are cytotoxic with respect to melanocytes, which could cause permanent depigmentation of the skin.

It therefore appears to be advantageous, for an application in humans, to have novel tyrosinase-inhibiting compounds that are both highly effective and exhibit good tolerance.

Of late, the use of double-stranded RNA, dsRNA, oligonucleotides, and more particularly of siRNA oligonucleotides (of 12 to 40 nucleotides), would make it possible to obtain a specific activity in the cosmetic field, such as skin care or hair care, but also in the dermatological and pharmaceutical fields.

However, the use of siRNAs in vivo is known to present various difficulties.

Besides the problem of the penetration of these siRNAs in order to reach the target cells when they are applied topically, due in particular to the difficulty in crossing the stratum corneum, experience has shown that the administration of siRNAs could bring about the triggering of an interferon response reported by numerous publications (Sledz C A et al., Activation of the interferon system by short-interfering RNA., Nat Cell Biol., 2003; 9:834-9. Katalin Karikó et al., Small Interfering RNAs Mediate Sequence-Independent Gene Suppression and Induce Immune Activation by Signaling through Toll-Like Receptor 31, J. Immunol., 2004; 172: 6545-6549. Judge A D et al., Sequence-dependent stimulation of the mammalian innate immune response by synthetic siRNA, Nat. Biotechnol., 2005; 23:457-62) and also the induction or the inhibition of the expression of genes not targeted by the siRNA (Jackson et al., Expression profiling reveals off-target gene regulation by RNAi, Nat. Biotechnol., 2003; 21:635-7), these two phenomena are highly undesirable.

Published U.S. Application No. 2004/0215006 describes double-stranded and anti-sense single-stranded RNA oligonucleotides which are active against tyrosinase; the examples relate only to anti-sense single-stranded RNA oligonucleotides. In particular, it is not demonstrated whether the siRNAs homologous to these anti-sense RNAs are effective.

Some authors have emphasized that double-stranded RNA oligonucleotides, such as siRNAs, and anti-sense single-stranded RNA oligonucleotides have different targets and that the activity of an anti-sense RNA cannot be extrapolated to the siRNA of the same sequence (Xu et al., Effective small interfering RNAs and phosphorothioate anti-sense DNAs have different preferences for target sites in the luciferase mRNAs, BBRC 2003; 306:712-717).

Moreover, in said 2004/0215006, the concentrations of siRNA proposed are from 50 and 200 nM. As indicated above, Jackson et al., have described a strong positive and negative regulation of genes not targeted by the siRNAs used at concentrations of 100 nM.

Similarly, in WO 2005/060536, which describes siRNAs that specifically inhibit tyrosinase, the concentration ranges proposed are very wide and can result in compositions comprising a very large amount of siRNAs for which a positive and negative regulation of genes not targeted by the siRNAs may be observed.

In the context of a cosmetic or therapeutic use, this regulation of non-targeted genes is not acceptable, in particular due to its unpredictable nature.

SUMMARY OF THE INVENTION

Novel siRNAs have now been developed that specifically inhibit tyrosinase expression from which siRNAs have been selected which exhibit an activity such that the siRNAs can be used at a dose of less than or equal to 1 nM.

In addition to solving the problems related to the induction of nonspecific genes, it has now been verified that these sequences of siRNAs do not induce an interferon response.

For this, the expression was measured of the OAS-1 and IFIT-1 (interferon-inducible tetratricopeptide repeat domain) genes known to be induced by interferon (Stefan F. Wieland et al., Searching for Interferon-Induced Genes that inhibit Hepatitis B Virus Replication in Transgenic Mouse Hepatocytes, J. of Virology 2003, 77:1227-1236) according to the protocol described in the manual of the "BLOCK-iT™ RNAi Stress Response Control Kit (Human) for monitoring interferon-mediated stress response to double-stranded RNA in human cells" marketed by Invitrogen.

Furthermore, the association of these tyrosinase-specific siRNAs with cationic particles less than or equal to 1 μm in size, with a zeta potential of 10 to 80 mV, makes it possible to very significantly improve their penetration into the target cells of a three-dimensional model such as the skin. Once penetrated, the tyrosinase-specific siRNA becomes active.

The penetration can be evaluated by means of a fluorescent label attached to the siRNA and its activity can be evaluated by quantifying the targeted messenger by quantitative PCR or by assaying the protein corresponding to the targeted messenger.

The cationic particles of the invention may be surfactant micelles, micelles of block or non-block polymers, cationic liposomes and niosomes, cationic oleosomes, cationic nanoemulsions, and also cationic organic or inorganic particles and nanocapsules.

Thus, the present invention features a double-stranded RNA oligonucleotide (also called dsRNA or siRNA) selected from among the oligonucleotides of sequence SEQ ID NOS. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48, optionally modified.

The use of dsRNA and, more particularly, of siRNA (for short interfering RNA) makes it possible to obtain an activity of specific inhibition of the synthesis of a target protein by degradation of the mRNA encoding the protein. The degradation of the target mRNA is obtained through the activation of the RISC complex (RNA Induced Silencing Complex) which has its effect through the binding of the anti-sense strand of the dsRNA to the mRNA (see Tuschl T. Chem. Biochem., 2001; 2:239-245; Nykanen A & al, Cell 2001; 107:309-321; Dorsett Y. and Tuschl T. Nat Rev Drug Discov., 2004; 3:318-329; Downward J. BMJ. 2004; 328:1245-1248; Shanker P. et al., JAMA 2005; 293:1367-1373).

The molecular mechanism implemented involves double-stranded RNA fragments consisting of 12 to 40 nucleotides, preferably of 23 to 27 nucleotides.

These double-stranded RNA oligonucleotides can preferably be composed of a homologous sense strand and of an anti-sense strand complementary to the sequence of the mRNA of human tyrosinase (GenBank accession number NM_000372). The double-stranded RNA oligonucleotide has blunt ends or unpaired ends of 2 to 6 nucleotides.

The double-stranded RNA oligonucleotides can be synthesized according to numerous manual or automatic, in vivo or in vitro synthesis methods.

The in vitro synthesis methods may be chemical or enzymatic, for example using an RNA polymerase (by way of example, T3, T7 or SP6) which will carry out the transcription of a selected DNA (or cDNA) sequence model.

DETAILED DESCRIPTION OF BEST MODE AND SPECIFIC/PREFERRED EMBODIMENTS OF THE INVENTION

Numerous methods for the in vivo synthesis of double-stranded RNA are described in the literature; they can be carried out in various bacterial cell types or cell types from higher organisms (Sambrook et al., Molecular Cloning, A Laboratory Manual, Second Edition (1989), DNA cloning, volume I and II, D. N. Glover (ed. 1985), Oligonucleotide Synthesis, M. J. Gaits (ed. 1984), Nucleic Acid Hybridation, B. D. Hames and S. J. Higgins (ed. 1984), Transcription and Translation B. D. Hames and S. J. Higgins (ed. 1984), Animal Cell Culture, R. I. Freshney (ed. 1986), Immobilized Cells and Enzymes, IRL Press (1986), B. Pertal, A Practical Guide to Molecular Cloning (1984), Gene Transfer Vectors for Mammalian Cells, J. H. Miller and M. P. Calos, Cold Spring Harbor Laboratory (ed. 1987), Methods in Enzymology, vol. 154, Wu and Grossman, and 155, Wu, Mayer and Walker (1987), Immunochemical Methods in Cell and Molecular Biology, Academic Press, London, Scopes (1987), Protein Purification: Principle and Practice, 2nd ed., Springer-Verlag, N.-Y. and Handbook of Experimental Immunology, vol. I-IV, C. D. Weir and C. C. Blackwell (1986)). Reference may also be made to the synthesis methods described in WO 01/36646, WO 01/75164 and U.S. Patent Published Application No. 2003/0088087.

Preferably, the double-stranded RNA oligonucleotides according to the invention are modified through the addition of an —O-methyl group in the 2'-position.

The double-stranded RNA oligonucleotides can be subjected to various modifications, they can in particular be modified as described in Published U.S. Application No. 2004/014956.

Advantageously, the modifications will result in double-stranded RNA oligonucleotides which are more stable, and, more preferably, double-stranded RNA oligonucleotides which have been rendered furtive with respect to the interferon response; this property is essential for use in vivo. The double-stranded RNA oligonucleotides may also have a sense sequence modified in such a way that it cannot be incorporated into the RISC and therefore cannot induce side effects.

Preferably, the double-stranded RNA oligonucleotides of SEQ ID NOS. 1, 2, 4, 13, 16, 35, 37, 40 and 42, having a tyrosinase mRNA degradation efficiency of greater than 50% at 0.016 nM, measured according to the protocol of Example 2 hereinafter, will be used.

The subject of the present invention also relates to a composition comprising at least one double-stranded RNA oligonucleotide selected from among the oligonucleotides of sequence SEQ ID NOS. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48.

In this composition, the double-stranded RNA oligonucleotide is present at a concentration of less than or equal to 100 μM, preferably less than or equal to 10 μM, and more preferably less than or equal to 1 μM.

The compositions according to the invention are preferably suitable for topical administration to the surface of the body, i.e., the skin, the integuments, the mucous membranes and the eyes.

In a preferred embodiment of the present invention, the double-stranded RNA oligonucleotides are associated with a cationic particle less than or equal to 1 μm in size, with a zeta potential of from 10 to 80 mV.

In this embodiment, the double-stranded RNA oligonucleotides will adhere to the surface of the particle, the latter serving as a carrier to cause it to penetrate into the structures of the skin and into the target cells of the skin, of the mucous membranes or else of the eyes for cosmetic, dermatological and/or ophthalmic applications.

The cationic particles according to the invention are particles that are less than or equal to 1 μm, preferably less than or equal to 500 nm, more preferably less than or equal to 300 nm, in size, it being possible to measure said size with, for example, a laser particle sizer type BI90 plus from the company Brookhaven, and that have a zeta potential of from 10 to 80 mV which can be measured with a zetameter type DELSA 440 from the company Coultronics.

The cationic particle can be selected from surfactant micelles, in particular micelles of nonionic amphiphilic surfactants and of cationic surfactants, block polymer micelles, in particular micelles of a cationic amphiphilic block polymer, micelles of a nonionic amphiphilic block polymer and of a cationic amphiphilic block polymer and micelles of a nonionic amphiphilic block polymer and of a cationic surfactant, liposomes of nonionic and cationic surfactants, niosomes, oleosomes, particles of nanoemulsions, nanocapsules, organic particles or inorganic particles.

Listed below, and in a non-exhaustive manner, are cationic particles which can be used according to the invention.

Surfactant Micelles:

To recall, micelles are aggregates that are spontaneously formed by amphiphilic molecules when they are solubilized in water or oil, beyond a certain concentration referred to as critical: the CMC.

The micelles which can be used in the context of the invention include at least one cationic surfactant. This cationic surfactant can be associated with one or more nonionic amphiphilic surfactants.

Those skilled in the art will advantageously select the nonionic and cationic surfactants from McCutcheons 1998 "emulsifiers and detergents" and from the subsequent editions.

By way of non-limiting examples, the cationic surfactants which can be used in the context of the invention are listed hereinafter.

Without this being limiting, the nonionic surfactants which can be used are: alkyl and polyalkyl (C6 to C30, saturated or unsaturated, branched or unbranched) esters or ethers of PEO, of glycerol and of polyglycerol, of sorbitan which may or may not be oxyethylenated, of sucrose, of glucose which may or may not be oxyethylenated, of maltose, of PPO-PEO.

In the case of a mixture between nonionic surfactants and cationic surfactants, the respective proportions thereof, by weight, will be from 99/1 and 1/99.

The amount of surfactants forming the micelles will be dependent on the CMC of the latter. However, in the context of the invention, the concentration of micellar surfactants will range from 0.1 to 10%, and preferably from 0.2 to 5%, by weight relative to the total weight of the composition.

Block Polymer Micelles:

The micelles of amphiphilic block polymers can be prepared according to the method described in WO 04/035013.

The block copolymers used for the preparation of the micelles associated with the dsRNAs according to the invention are in particular amphiphilic block polymers which are preferably nonionic, diblock or triblock, and which can form micelles on contact with water. They are in particular of diblock (A-B) or triblock (A-B-A) type, A corresponding to a nonionic hydrophilic polymeric block and B to a hydrophobic polymeric block. The molecular weight of the polymers can be from 1000 and 100 000 and the A/B ratio can be from 1/100 and 50/1.

In the context of the invention, three types of micelles can be used:
  micelles of a cationic amphiphilic block polymer;
  mixed micelles of a nonionic amphiphilic block polymer associated with a cationic amphiphilic block polymer; and
  mixed micelles of a nonionic amphiphilic block polymer associated with a cationic surfactant.

The nonionic hydrophilic polymeric block can be selected from polyethylene oxide (PEO) and polyvinylpyrrolidone (PVP).

The hydrophobic polymeric block can be selected from polystyrene, poly(tert-butylstyrene), poly(methyl methacrylate), poly(ethyl acrylate), poly(butyl acrylate), poly(butyl methacrylate), poly(vinyl acetate), polycaprolactones, polycaprolactams, polydimethylsiloxanes, poly($C_3$-$C_6$ alkylene oxide)s, poly(aspartic acid), poly(lactic acid), poly(glycolic acid), polyleucine, polybutadienes, polyethylenes, polypropylenes, polybutylenes.

The block copolymer is preferably selected from among the following block copolymers:
  polypropylene oxide/polyethylene oxide
  polystyrene/polyoxyethylene
  poly(methyl methacrylate)/polyoxyethylene
  poly(butyl methacrylate)/polyoxyethylene
  polyoxybutylene/polyoxyethylene
  polycaprolactone/polyoxyethylene
  polyethylene/polyoxyethylene
  polyoxyethylene/polyoxybutylene/polyoxyethylene.

In the context of the invention, it is necessary to add to the micellar composition:
  a cationic amphiphilic block polymer, one of the blocks of which is cationic and can be selected, by way of example, from among:
    poly(trimethylethylammonium methacrylate);
    quaternized poly(dimethylaminoethyl methacrylate);
    polymethylvinylimidazolium;
    poly(vinylbenzyltrimethylammonium chloride).

The association of a nonionic amphiphilic block polymer with a cationic amphiphilic block polymer is such that the ratio between the two will range from 99/1 to 1/99; and/or at least one cationic surfactant as listed hereinafter.

In this case, the respective ratio of the nonionic amphiphilic block polymer to the cationic surfactant will range from 50/50 to 99/1.

In the context of the invention, the concentration of micellar block polymers, which may or may not be associated with a cationic surfactant, will range from 0.1 to 10%, and preferably from 0.2 to 5%, by weight relative to the total weight of the composition.

In one embodiment of the invention, it is also possible to form micelles consisting of cationic amphiphilic block polymers as described above.

Liposomes and Niosomes:

The nonionic amphiphilic lipids capable of forming nonionic liposomes are in particular those described in EP-0-582, 503.

In particular, the nonionic amphiphilic lipids can be a mixture of esters of at least one polyol selected from the group consisting of polyethylene glycol having from 1 to 60 ethylene oxide units, sorbitan, sorbitan bearing 2 to 60 ethylene oxide units, glycerol bearing 2 to 30 ethylene oxide units, polyglycerols containing 2 to 15 glycerol units, sucroses, glucoses bearing 2 to 30 ethylene oxide units, and of at least one fatty acid containing a linear or branched, saturated or unsaturated $C_5$-$C_{17}$ alkyl chain, the number of alkyl chains per polyol group ranging from 1 to 10.

The expression "mixture of esters" covers not only mixtures of pure esters of different chemical families, but also covers any product which contains several chemically pure esters of a polyol of the same family in variable proportions. This is, in particular, the case of products having a statistical formula, in their hydrophilic portion, for example a polyglyceryl ester of formula $CO-(OCH_2-CHOH-CH_2)_n-OH$ where n is a statistical value and which can contain various proportions of esters for which n=1, n=2, n=3, n=4, etc.; it is also the case of esters containing several alkyl chains in their lipophilic portion, such as cocoates, which contain $C_5$ to $C_{17}$ alkyl chains, or isostearates, where the $C_{17}$ alkyl chains are a complex mixture of isomeric forms; it is also the case of products consisting of mixtures of mono-, di-, tri- or polyesters of the same polyol. It should be noted that a product which contains only a single ester capable of forming vesicles and impurities of another type cannot be used according to the invention.

Commercial esters which can be used alone according to the invention, because they are in reality mixtures of esters, are, for example, as follows:
- the partial esters of sorbitan (or sorbitol anhydride) and of a fatty acid, marketed under the trademarks "SPAN 20, 40, 60 and 80" by "ICI";
- the sorbitan isostearate marketed under the trademark "SI 10 R NIKKOL" by "NIKKO";
- the sorbitan stearate bearing 4 ethylene oxide units, marketed under the trademark "TWEEN 61" by "ICI";
- the polyethylene glycol stearate containing 8 ethylene oxide units, marketed under the trademark "MYR J 45" by "ICI";
- the polyethylene glycol monostearate of formula EMI6.1, in which formula n is equal to 4, marketed under the trademark "MYS 4" by "NIKKO";
- the polyethylene glycol stearate, molecular weight 400, chemical quality or quality produced by biotechnology, marketed by "UNICHEMA";
- the diglyceryl stearate bearing 4 ethylene oxide units, marketed under the trademark "HOSTACERINE DGS" by "HOECHST";
- the tetraglyceryl stearate marketed under the trademark "TETRAGLYN 1S" by "NIKKO";
- the diglyceryl isostearate, marketed by "SOLVAY";
- the diglyceryl distearate marketed under the trademark "EMALEX DSG 2" by "NIHON";
- the sucrose mono-, di- and tripalmitostearates marketed under the trademarks "F50, F70, F110 and F160 CRODESTA" by "CRODA";
- the mixture of sucrose monopalmitostearate and sucrose dipalmitostearate, marketed under the trademark "GRILLOTEN PSE 141 G" by "GRILLO";
- the mixture of sucrose stearate and sucrose cocoate, marketed under the trademark "ARLATONE 2121" by "ICI";
- the methylglucose distearate bearing 20 ethylene oxide units, marketed under the trademark "GLUCAM E 20 DISTEARATE" by "AMERCHOL".

Mixtures of these products, which are already mixtures, with one another, or mixtures of these products with pure products can, of course, be used.

The cationic surfactants are advantageously selected from the list hereinafter and such that they confer on the dispersion a pH of from 5 to 8; the weight ratio of the amount of nonionic amphiphilic lipids to the amount of cationic surfactants in the lipid phase being from 50/1 to 50/25, and the weight ratio of the lipid phase to the aqueous phase of a dispersion being from 1/1000 to 300/1000.

Oleosomes:

The oleosomes relating to the invention are described in EP-0-705,593. They involve an emulsion of the oil-in-water type made up of oily globules provided with a lamellar liquid crystal coating, dispersed in an aqueous phase, characterized in that each oily globule is, as a unit, coated with a monolamellar or oligolamellar layer (1 to 10 sheets that can be visualized by transmission electron microscopy after cryofracture) obtained from at least one lipophilic surfactant, at least one hydrophilic surfactant and at least one cationic surfactant conferring on the emulsion a pH ranging from 5 to 8, the coated oily globules having an average diameter of less than 500 nanometers.

The lipophilic surfactant and the hydrophilic surfactant each contain at least one saturated fatty chain having more than approximately 12 carbon atoms. Even more preferably, this fatty chain contains from 16 to 22 carbon atoms.

According to another preferred embodiment of the invention, the lipophilic surfactant has an HLB of from approximately 2 to approximately 5. As is well known, the term HLB (Hydrophilic-Lipophilic Balance) means the balance between the size and the strength of the hydrophilic group and the size and the strength of the lipophilic group of the surfactant.

Examples of such lipophilic surfactants are sucrose distearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the glyceryl ester of palmitic acid and stearic acid, polyoxyethylenated monostearate 2 OE (comprising 2 oxyethylene units), glyceryl monobehenate and dibehenate, and pentaerythritol tetrastearate.

The hydrophilic surfactant preferably has an HLB of from approximately 8 to approximately 12.

As examples of such hydrophilic surfactants, mention may be made of the following compounds: polyoxyethylenated sorbitan monostearate 4 OE, polyoxyethylenated sorbitan tristearate 20 OE, polyoxyethylenated monostearate 8 OE, hexaglyceryl monostearate, polyoxyethylenated monostearate 10 OE, polyoxyethylenated distearate 12 OE and polyoxyethylenated methylglucose distearate 20 OE.

The cationic surfactants can advantageously be selected from among the compounds mentioned hereinafter.

Nanoemulsions:

The cationic particles can also be selected from oil-in-water nanoemulsions comprising an oily phase dispersed in an aqueous phase, the oil globules of which have a number-average size of less than 100 nm, characterized in that they comprise at least one amphiphilic lipid comprising at least one nonionic amphiphilic lipid and a cationic amphiphilic lipid, the oily phase and the amphiphilic lipids being present at a content such that the oily phase/amphiphilic lipid weight ratio ranges from 3 to 10.

The nanoemulsions generally have a transparent to bluish appearance. The transparency of said nanoemulsions is measured by means of a coefficient of transmittance at 600 nm ranging from 10 to 90%, or else by means of turbidity. The turbidity of the compositions of the invention ranges from 60 to 400 NTU, and preferably from 70 to 300 NTU, which turbidity is measured using a HACH portable turbidity meter—model 2100 P at approximately 25° C.

The oil globules of the nanoemulsions of the invention have a number-average size of less than 100 nm, and preferably ranging from 20 to 80 nm, and more preferably from 40 to 60 nm. Decreasing the size of the globules makes it possible to promote penetration of the active agents into the superficial layers of the skin (carrier effect).

The nanoemulsions in accordance with the invention are preferably prepared at temperatures ranging from 4 to 45° C. and are thus compatible with thermosensitive active agents.

These dispersions are in particular described in the following applications: EP-0-728,460, EP-0-879,589, EP-1-010,413, EP-1-010,414, EP-1-010,416, EP-1-013,338, EP-1-016,453, EP-1-018,363, EP-1-025,898 and EP-1-120,102. In all of these applications, it is specified that, in order to improve particle stability, an ionic surfactant will be added to the nonionic surfactant (or mixture).

In the case of the present application, one or more cationic surfactants will be exclusively used as ionic surfactant.

The proportions indicated in the references above are to be conserved and, by way of example of a cationic surfactant, the list common to all the particles will be selected.

The nonionic surfactants, preferably water-soluble or water-dispersible, contain at least one hydrophobic block and at least one hydrophilic block.

The nonionic amphiphilic lipids of the invention are preferably selected from among:
1/silicone surfactants,
2/amphiphilic lipids which are liquid at a temperature less than or equal to 45° C., selected from esters of at least one polyol or at least one fatty acid containing at least one linear or branched, saturated or unsaturated, and in particular unsaturated or branched, $C_8$-$C_{22}$ alkyl chain, the polyol being selected from the group consisting of polyethylene glycol having from 1 to 60 ethylene oxide units, sorbitan, glycerol which may contain from 2 to 30 ethylene oxide units, and polyglycerols having from 2 to 15 glycerol units,
3/esters of a fatty acid and of a sugar and ethers of a fatty alcohol and of a sugar,
4/surfactants which are solid at a temperature equal to 45° C., selected from among glycerol fatty esters, sorbitan fatty esters and oxyethylenated sorbitan fatty esters, ethoxylated fatty ethers and ethoxylated fatty esters,
5/block copolymers of ethylene oxide (A) and of propylene oxide (B), and mixtures of these surfactants.

1/The silicone surfactants which can be used according to the invention are silicone compounds containing at least one oxyethylenated chain —$OCH_2CH_2$— and/or oxypropylenated chain —$OCH_2CH_2CH_2$—; exemplary are those described in U.S. Pat. Nos. 5,364,633 and 5,411,744.

Preferably, the silicone surfactant used according to the present invention is a compound of formula (II):

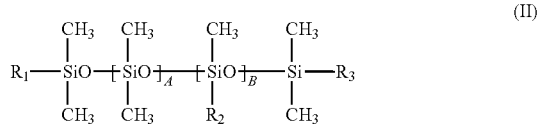

(II)

in which:

$R_1$, $R_2$ and $R_3$, independently of one another, represent a $C_1$-$C_6$ alkyl radical or a —$(CH_2)_x$—$(OCH_2CH_2)_y$—$(OCH_2CH_2CH_2)_n$—$OR_4$ radical, at least one radical $R_1$, $R_2$ or $R_3$ not being an alkyl radical; $R_4$ being hydrogen, an alkyl radical or an acyl radical;

A is an integer ranging from 0 to 200;
B is an integer ranging from 0 to 50; with the proviso that A and B are not equal to zero at the same time;
x is an integer ranging from 1 to 6;
y is an integer ranging from 1 to 30;
z is an integer ranging from 0 to 5.

According to another preferred embodiment of the invention, in the compound of formula (X), the alkyl radical is a methyl radical, x is an integer ranging from 2 to 6 and y is an integer ranging from 4 to 30.

By way of example of silicone surfactants of formula (II), representative are the compounds of formula (III):

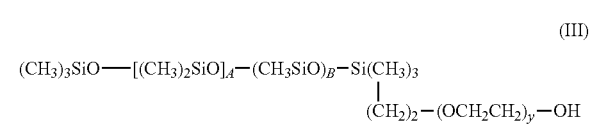

(III)

in which A is an integer ranging from 20 to 105, B is an integer ranging from 2 to 10 and y is an integer ranging from 10 to 20.

By way of example of silicone surfactants of formula (II), mention may also be made of the compounds of formula (IV):

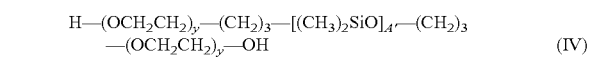

(IV)

in which A' and y are integers ranging from 10 to 20.

As silicone surfactants, use may particularly be made of those marketed by Dow Corning under the trademarks DC 5329, DC 7439-146, DC 2-5695 and Q4-3667. The compounds DC 5329, DC 7439-146 and DC 2-5695 are compounds of formula (XI) where, respectively, A is 22, B is 2 and y is 12; A is 103, B is 10 and y is 12; A is 27, B is 3 and y is 12.

The compound Q4-3667 is a compound of formula (IV) where A is 15 and y is 13.

2/The amphiphilic lipids which are liquid at a temperature less than or equal to 45° C. can in particular be selected from among:
the polyethylene glycol isostearate of molar weight 400 (CTFA name: PEG-8 Isostearate), marketed under the trademark Prisorine 3644 by UNICHEMA;
the diglyceryl isostearate marketed by SOLVAY;
the polyglyceryl laurate containing 2 glycerol units (polyglyceryl-2 laurate), marketed under the trademark Diglycerin-monolaurate by SOLVAY;
the sorbitan oleate marketed under the trademark SPAN 80 by ICI;
the sorbitan isostearate marketed under the trademark NIKKOL SI 10R by NIKKO;
the α-butylglucoside cocoate or the α-butylglucoside caprate marketed by ULICE.

3/The esters of a fatty acid and of a sugar, which can be used as nonionic amphiphilic lipids in a nanoemulsion according to the invention, are preferably solid at a temperature of less than or equal to 45° C. and can be selected in particular from among the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose.

The $C_8$-$C_{22}$ or $C_{14}$-$C_{22}$ fatty acids which form the fatty unit of the esters which can be used in the nanoemulsion of the invention contain a saturated or unsaturated linear alkyl chain having, respectively, from 8 to 22 or from 14 to 22 carbon atoms. The fatty unit of the esters can in particular be selected from stearates, behenates, arachidonates, palmitates, myristates, laurates, caprates and mixtures thereof. Stearates are preferably used.

By way of example of esters or of mixtures of esters of a fatty acid and of sucrose, of maltose, of glucose or of fructose, representative are sucrose monostearate, sucrose distearate, sucrose tristearate and mixtures thereof, such as the products marketed by Croda under the trademark Crodesta F50, F70, F110 and F160 having, respectively, an HLB (Hydrophilic-Lipophilic Balance) of 5, 7, 11 and 16; and by way of example of esters or of mixtures of esters of a fatty acid and of methylglucose, mention may be made of polyglyceryl-3 methylglucose distearate, marketed by Goldschmidt under the trademark Tego-care 450. Mention may also be made of monoesters of glucose or of maltose such as methyl o-hexadecanoyl-6-D-glucoside and o-hexadecanoyl-6-D-maltoside.

The ethers of a fatty alcohol and of a sugar, which can be used as nonionic amphiphilic lipids in the nanoemulsion according to the invention, are solid at a temperature of less than or equal to 45° C. and can be selected in particular from among the group comprising ethers or mixtures of ethers of a $C_8$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols which form the fatty unit of the ethers which can be used in the nanoemulsion of the invention contain a saturated or unsaturated linear alkyl chain having, respectively, from 8 to 22 or from 14 to 22 carbon atoms. The fatty unit of the ethers can in particular be selected from decyl, cetyl, behenyl, arachidyl, stearyl, palmityl, myristyl, lauryl, capryl and hexadecanoyl units, and mixtures thereof such as cetearyl.

By way of example of ethers of a fatty alcohol and of a sugar, mention may be made of alkylpolyglucosides such as decylglucoside and laurylglucoside, marketed, for example, by Henkel under the respective trademarks Plantaren 2000 and Plantaren 1200, cetostearylglucoside optionally as a mixture with cetostearyl alcohol, marketed, for example, under the trademark Montanov 68 by Seppic, under the trademark Tego-care CG90 by Goldschmidt and under the trademark Emulgade KE3302 by Henkel, and arachidylglucoside, for example in the form of the mixture of arachidyl and behenyl alcohols and of arachidylglucoside, marketed under the trademark Montanov 202 by Seppic.

As a nonionic amphiphilic lipid of this type, use is more particularly made of sucrose monostearate, sucrose distearate, sucrose tristearate and mixtures thereof, polyglyceryl-3 methylglucose distearate and alkylpolyglucosides.

4/The glycerol fatty esters which can be used as nonionic amphiphilic lipids in the nanoemulsion according to the invention, which are solid at a temperature of less than or equal to 45° C., can be selected in particular from the group comprising the esters formed from at least one acid containing a saturated linear alkyl chain having from 16 to 22 carbon atoms, and from 1 to 10 glycerol units. One or more of these glycerol fatty esters can be used in the nanoemulsion of the invention.

These esters can in particular be selected from among stearates, behenates, arachidates, palmitates and mixtures thereof. Stearates and palmitates are preferably used.

By way of example of a surfactant which can be used in the nanoemulsion of the invention, mention may be made of decaglyceryl (10 units of glycerol) monostearate, distearate, tristearate and pentastearate (CTFA names: Polyglyceryl-10 stearate, Polyglyceryl-10 distearate, Polyglyceryl-10 tristearate, Polyglyceryl-10 pentastearate), such as the products marketed under the respective trademarks Nikkol Decaglyn 1-S, 2-S, 3-S and 5-S by Nikko, and diglyceryl monostearate (CTFA name: Polyglyceryl-2 stearate) such as the product marketed by Nikko under the trademark Nikkol DGMS.

The sorbitan fatty esters which can be used as nonionic amphiphilic lipids in the nanoemulsion according to the invention, which are solid at a temperature of less than or equal to 45° C., are selected in particular from among the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid containing at least one saturated linear alkyl chain having respectively from 16 to 22 carbon atoms, and from sorbitol or ethoxylated sorbitol. The oxyethylenated esters generally contain from 1 to 100 ethylene oxide units, and preferably from 2 to 40 ethylene oxide (EO) units.

These esters can in particular be selected from among stearates, behenates, arachidates, palmitates, and mixtures thereof. Stearates and palmitates are preferably used.

By way of example of a sorbitan fatty ester and of an oxyethylenated sorbitan fatty ester, which can be used in the nanoemulsion of the invention, representative are the sorbitan monostearate (CTFA name: Sorbitan stearate) marketed by ICI under the trademark Span 60, the sorbitan monopalmitate (CTFA name: Sorbitan palmitate) marketed by ICI under the trademark Span 40, and the sorbitan tristearate 20 EO (CTFA name: Polysorbate 65) marketed by ICI under the trademark Tween 65.

The ethoxylated fatty ethers which are solid at a temperature of less than or equal to 45° C., which can be used as nonionic amphiphilic lipids in the nanoemulsion according to the invention, are preferably ethers formed from 1 to 100 ethylene oxide units and from at least one fatty alcohol chain having from 16 to 22 carbon atoms. The fatty chain of the ethers can in particular be selected from among behenyl, arachidyl, stearyl and cetyl units, and mixtures thereof such as cetearyl. By way of example of ethoxylated fatty ethers, mention may be made of ethers of behenyl alcohol comprising 5, 10, 20 and 30 ethylene oxide units (CTFA names: Beheneth-5, Beheneth-10, Beheneth-20, Beheneth-30), such as the products marketed under the trademarks Nikkol BB5, BB10, BB20 and BB30 by Nikko, and the ether of stearyl alcohol comprising 2 ethylene oxide units (CTFA name: Steareth-2), such as the product marketed under the trademark Brij 72 by ICI.

The ethoxylated fatty esters which are solid at a temperature of less than or equal to 45° C., which can be used as nonionic amphiphilic lipids in a nanoemulsion according to the invention, are esters formed from 1 to 100 ethylene oxide units and from at least one fatty acid chain having from 16 to 22 carbon atoms. The fatty chain of the esters can in particular be selected from among stearate, behenate, arachidate and palmitate units, and mixtures thereof. By way of example of ethoxylated fatty esters, mention may be made of the ester of stearic acid comprising 40 ethylene oxide units, such as the product marketed under the trademark Myrj 52 (CTFA name: PEG-40 stearate) by ICI and also the ester of behenic acid comprising 8 ethylene oxide units (CTFA name: PEG-8 behenate), such as the product marketed under the trademark Compritol HD5 ATO by Gattefosse.

5/The block copolymers of ethylene oxide and of propylene oxide, which can be used as nonionic amphiphilic lipids in the nanoemulsion according to the invention, can be selected in particular from among the block copolymers of formula (V):

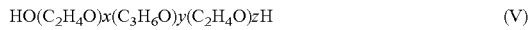
$$HO(C_2H_4O)x(C_3H_6O)y(C_2H_4O)zH \quad (V)$$

in which x, y and z are integers such that x+z ranges from 2 to 100 and y ranges from 14 to 60, and mixtures thereof, and more particularly from the block copolymers of formula (V) having an HLB ranging from 2 to 16.

These block copolymers can in particular be selected from among poloxamers, and in particular from Poloxamer 231 such as the product marketed by ICI under the trademark Pluronic L81 of formula (V) with x=z=6, y=39 (HLB 2); Poloxamer 282 such as the product marketed by ICI under the trademark Pluronic L92 of formula (V) with x=z=10, y=47 (HLB 6); and Poloxamer 124 such as the product marketed by ICI under the trademark Pluronic L44 of formula (V) with x=z=11, y=21 (HLB 16).

As nonionic amphiphilic lipids, representative are the mixtures of nonionic surfactants described in EP-A-705593, incorporated herein for reference.

Among the nonionic amphiphilic lipids, use may in particular be made of:
- PEG 400 isostearate or PEG-8 isostearate (containing 8 mol of ethylene oxide),
- diglyceryl isostearate,
- polyglyceryl monolaurate containing 2 units of glycerol and polyglyceryl stearates containing 10 units of glycerol,
- sorbitan oleate,
- sorbitan isostearate, and mixtures thereof.

The nonionic amphiphilic lipids can be present in the nanoemulsion according to the invention at a content ranging from 0.2% to 12% by weight, relative to the total weight of the composition, and preferably ranging from 0.2% to 8% by weight, and preferentially ranging from 0.2% to 6% by weight.

The cationic amphiphilic lipids are selected from the list given hereinafter.

They are present in the nanoemulsions of the invention, preferably, in concentrations ranging from 0.01 to 6% by weight relative to the total weight of the nanoemulsion, and more particularly from 0.2 to 4% by weight.

Oils:

The oily phase of the nanoemulsions according to the invention comprise at least one oil. The oils which can be used in the nanoemulsions of the invention are preferably selected from the group consisting of:
- oils of animal or plant origin, made up of esters of fatty acids and of polyols, in particular liquid triglycerides, for example sunflower oil, corn oil, soybean oil, avocado oil, jojoba oil, marrow oil, grapeseed oil, sesame seed oil, hazelnut oil, fish oils and glyceryl tricaprocaprylate, or plant or animal oils of formula $R_9COOR_{10}$ in which $R_9$ is a higher fatty acid residue having from 7 to 29 carbon atoms and $R_{10}$ is a linear or branched hydrocarbon-based chain having from 3 to 30 carbon atoms, in particular alkyl or alkenyl, for example purcellin oil or liquid jojoba wax;
- natural or synthetic essential oils, such as, for example, eucalyptus oil, lavandin oil, lavender oil, vetiver oil, litsea cubeba oil, lemon oil, sandlewood oil, rosemary oil, camomile oil, savoury oil, nutmeg oil, cinnamon oil, hyssop oil, caraway oil, orange oil, geraniol oil, cade oil and bergamot oil;
- synthetic oils such as parleam oil, polyolefins and liquid carboxylic acid esters;
- mineral oils such as hexadecane, isohexadecane and paraffin oil;
- halogenated oils, in particular fluorocarbons such as fluoroamines, for example perfluorotributylamine, fluorohydrocarbons, for example perfluorodecahydronaphthalene, fluoro esters and fluoro ethers;
- volatile or non-volatile silicone oils.

The polyolefins which can be used as synthetic oils are in particular poly-α-olefins, and more particularly those of hydrogenated or non-hydrogenated polybutene type, and preferably hydrogenated or non-hydrogenated polyisobutene type.

The liquid carboxylic acid esters which can be used as synthetic oils may be monocarboxylic, dicarboxylic, tricarboxylic, or tetracarboxylic acid esters. The total number of carbons in the esters is generally greater than or equal to 10, and preferably less than 100, and more particularly less than 80. They are in particular monoesters of saturated or unsaturated, linear or branched $C_1$-$C_{26}$ aliphatic acids and of saturated or unsaturated, linear or branched $C_1$-$C_{26}$ aliphatic alcohols, the total number of carbons in the esters generally being greater than or equal to 10. Use may also be made of esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{25}$ dihydroxy, trihydroxy, tetrahydroxy or pentahydroxy alcohols.

Among the esters mentioned above, use is preferably made of alkyl palmitates such as ethyl palmitate, isopropyl palmitate, 2-ethylhexyl palmitate, 2-octyldecyl palmitate; alkyl myristates such as isopropyl myristate, butyl myristate, cetyl myristate, 2-octyldodecyl myristate; alkyl stearates such as hexyl stearate, butyl stearate, isobutyl stearate; alkyl malates such as dioctyl malate; alkyl laurates such as hexyl laurate and 2-hexyldecyl laurate; isononyl isononanoate; cetyl octanoate.

Advantageously, the nanoemulsions according to the invention contain at least one oil of molecular weight greater than or equal to 400, in particular ranging from 400 to 10 000, better still ranging from 400 to 5000, or even ranging from 400 to 2500. The oils of molecular weight greater than or equal to 400 can be selected from oils of animal or plant origin, mineral oils, synthetic oils and silicone oils, and mixtures thereof. As oils of this type, mention may, for example, be made of isocetyl palmitate, isocetyl stearate, avocado oil and jojoba oil.

The nanoemulsions in accordance with the invention comprise an amount of oily phase (oil and other fatty substances besides the amphiphilic lipid) preferably ranging from 2 to 40% by weight relative to the total weight of the nanoemulsion, and more particularly from 4 to 30% by weight, and preferably from 4 to 20% by weight.

The oily phase and the amphiphilic lipids (nonionic and ionic amphiphilic lipids) are preferably present in the nanoemulsions according to the invention according to a weight ratio of the amount of oily phase to the amount of amphiphilic lipid ranging from 3 to 10, and preferably ranging from 3 to 6. The term "amount of oily phase" means the total amount of the constituents of this oily phase without including the amount of amphiphilic lipid. The nanoemulsions in accordance with the present invention can contain, in addition to the urea derivatives of formula (I) described above, solvents, in particular for improving, if necessary, the transparency of the composition.

These solvents are preferably selected from the group consisting of:
C$_1$-C$_8$ lower alcohols such as ethanol;
glycols such as glycerol, propylene glycol, 1,3-butylene glycol, dipropylene glycol, or polyethylene glycols having from 4 to 16 ethylene oxide units, and preferably from 8 to 12;
sugars such as glucose, fructose, maltose, lactose or sucrose.

These solvents can be used as a mixture. When they are present in the nanoemulsions of the invention, they can be used at concentrations preferably ranging from 0.01 to 30% by weight relative to the total weight of the nanoemulsion, and better still from 5 to 20% by weight relative to the total weight of the nanoemulsion. The amount of alcohol(s) and/or of sugar(s) preferably ranges from 5 to 20% by weight relative to the total weight of the nanoemulsion and the amount of glycol(s) preferably ranges from 5 to 15% by weight relative to the total weight of the nanoemulsion.

Method of Preparation:

The method of preparing a nanoemulsion as defined above entails mixing the aqueous phase containing the urea derivative and the oily phase, with vigorous stirring, at a temperature ranging from 10° C. to 80° C., and in carrying out a high-pressure homogenization step at a pressure of greater than $5\times10^7$ Pa and in optionally adding the polymer used. According to a preferred embodiment of the invention, another high-pressure homogenization step is subsequently carried out at a pressure of greater than $5\times10^7$ Pa. The high-pressure homogenization is preferably carried out at a pressure ranging from $6\times10^7$ Pa to $18\times10^7$ Pa. The shear preferably ranges from $2\times10^6$ s$^{-1}$ to $5\times10^8$ S$^{-1}$, and better still from $1\times10^8$ s$^{-1}$ to $3\times10^8$ s$^{-1}$ (s$^{-1}$ signifies second$^{-1}$). Such a method makes it possible to produce nanoemulsions compatible with thermosensitive active compounds, which may contain oils and in particular fragrances which contain fatty substances, without denaturing them.

Nanocapsules:

The nanocapsules relating to the invention are those described in EP-0-447,318, EP-0-557,489, EP-0-780,115, EP-1-025,901, EP-1-029,587, EP-1-034,839, EP-1-414,390, FR-2,830,776, EP-1-342,471, FR-2,848,879 and FR 04/50057.

The nanocapsules are Core-Shell particles having an oily core and a polymeric shell. The various applications mentioned above relate to various families of polymers and various methods for obtaining them. The size of the capsules is always less than 1 μm and it is possible to have sizes of less than 80 nm. These particles can be coated with a lamellar liquid crystal phase most commonly consisting of a lecithin or of a dimethicone copolyol. The coating must be an amphiphilic lipid capable of spontaneously forming a lamellar liquid crystal phase on contact with water. It is to this amphiphilic lipid capable of forming a lamellar phase that the cationic surfactant which will confer on the particles (the nanocapsule) a positive zeta potential will be added. The weight ratio of the amphiphilic lipid forming the lamellar phase to the cationic surfactant will be from 99/1 and 75/25.

The cationic surfactants which can be used are those listed hereinafter.

Organic Particles:

The organic particles of the invention are solid nanospheres, which do not have an internal cavity, formed by various methods (dispersion in water, nanoprecipitation, microemulsion, etc.) and composed of at least one polymer or of at least one copolymer, or of a mixture thereof. The particle is cationic, with the zeta potential defined above, either because the polymer(s) or copolymer(s) is (are) cationic, or because it (they) is (are) nonionic and a cationic surfactant as described hereinafter is used. In relation to the polymer, the amount of cationic surfactant will be from 0 and 25%.

Inorganic Particles:

The cationic inorganic particles of the invention may, by way of example, be based on silica, TiO$_2$, ZnO, alumina, etc. By way of example, representative are alumina particles in a colloidal dispersion in water, such as the Nanomer 2 particles from Nalco. Clariant and Grace also provide particles of this type.

Cationic Surfactants which can be Used for the Preparation of the Cationic Particles of the Invention:

The cationic surfactants which can be used according to the invention are listed hereinafter, this list being non-limiting.

The cationic amphiphilic lipids are preferably selected from the group consisting of quaternary ammonium salts and fatty amines and their salts.

The quaternary ammonium salts are, for example:
those which have the following general formula (IV):

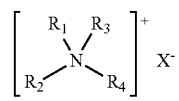

in which the radicals R$_1$ to R$_4$, which may be identical or different, represent a linear or branched aliphatic radical having from 1 to 30 carbon atoms, or an aromatic radical such as aryl or alkylaryl. The aliphatic radicals can contain heteroatoms such as, in particular, oxygen, nitrogen, sulfur or halogens. The aliphatic radicals are, for example, selected from among the following radicals: alkyl, alkoxy, polyoxy(C$_2$-C$_6$) alkylene, alkylamide, (C$_{12}$-C$_{22}$)alkylamido(C$_2$-C$_6$)alkyl, (C$_{12}$-C$_{22}$)alkyl acetate, hydroxyalkyl, containing approximately from 1 to 30 carbon atoms; X is an anion selected from the group consisting of halides, phosphates, acetates, lactates, (C$_2$-C$_6$)alkyl sulfates, and alkyl- or alkylarylsulfonates, quaternary ammonium salts of imidazolinium, such as, for example, that having the following formula (V):

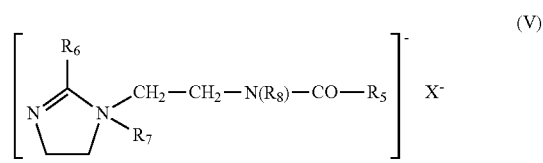

in which R$_5$ is an alkenyl or alkyl radical having from 8 to 30 carbon atoms, for example derived from tallow fatty acids, R$_6$ is a hydrogen atom, a C$_1$-C$_4$ alkyl radical or an alkenyl or alkyl radical having from 8 to 30 carbon atoms, R$_7$ is a C$_1$-C$_4$ alkyl radical, R$_8$ is a hydrogen atom or a C$_1$-C$_4$ alkyl radical, and X is an anion selected from the group consisting of halides, phosphates, acetates, lactates, alkyl sulfates, and alkyl- or alkylarylsulfonates. Preferably, R$_5$ and R$_6$ denote a mixture of alkenyl or alkyl radicals having from 12 to 21 carbon atoms, for example derived from tallow fatty acids, R$_7$ denotes methyl, and R$_8$ denotes hydrogen. Such a product is, for example, marketed under the trademark "REWOQUAT W 75" by REWO, quaternary diammonium salts having the formula (VI):

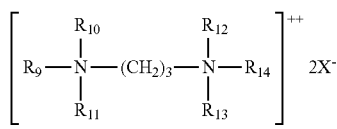

in which $R_9$ denotes an aliphatic radical containing approximately from 16 to 30 carbon atoms, $R_{10}$, $R_{11}$, $R_{12}$, $R_{13}$ and $R_{14}$, which may be identical or different, are selected from hydrogen or an alkyl radical having from 1 to 4 carbon atoms, and X is an anion selected from the group consisting of halides, acetates, phosphates, nitrates and methyl sulfates. Such quaternary diammonium salts comprise in particular propanetallowediammonium dichloride;

quaternary ammonium salts containing at least one ester function.

The quaternary ammonium salts containing at least one ester function which can be used according to the invention are, for example, those having the following formula (VII):

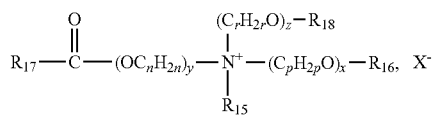

in which:

$R_{15}$ is selected from among $C_1$-$C_6$ alkyl radicals and $C_1$-$C_6$ hydroxyalkyl or dihydroxyalkyl radicals;

$R_{15}$ is selected from among:

the radical

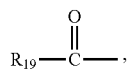

linear or branched, saturated or unsaturated $C_1$-$C_{22}$ hydrocarbon-based radicals $R_{20}$, a hydrogen atom, $R_{15}$ is selected from among:

the radical

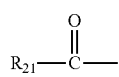

linear or branched, saturated or unsaturated $C_1$-$C_6$ hydrocarbon-based radicals $R_{22}$, a hydrogen atom, $R_{17}$, $R_{19}$ and $R_{21}$, which may be identical or different, are selected from among linear or branched, saturated or unsaturated $C_7$-$C_{21}$ hydrocarbon-based radicals;

n, p and r, which may be identical or different, are integers ranging from 2 to 6;

y is an integer ranging from 1 to 10;

x and z, which may be identical or different, are integers ranging from 0 to 10;

$X^-$ is a simple or complex organic or inorganic anion; with the proviso that the sum x+y+z is from 1 to 15, that when x is 0, then $R_{16}$ denotes $R_{20}$, and that when z is 0, then $R_{18}$ denotes $R_{22}$.

The alkyl radicals $R_{15}$ may be linear or branched, and more particularly linear.

Preferably, $R_{15}$ denotes a methyl, ethyl, hydroxyethyl or dihydroxypropyl radical, and more particularly a methyl or ethyl radical.

Advantageously, the sum x+y+z is from 1 to 10.

When $R_{16}$ is a hydrocarbon-based radical $R_{20}$, it may be long and may contain from 12 to 22 carbon atoms, or may be short and may contain from 1 to 3 carbon atoms.

When $R_{18}$ is hydrocarbon-based radical $R_{22}$, it preferably contains 1 to 3 carbon atoms.

Advantageously, $R_{17}$, $R_{19}$ and $R_{21}$, which may identical or different, are selected from among linear or branched, saturated or unsaturated $C_{11}$-$C_{21}$ hydrocarbon-based radicals, and more particularly from linear or branched, saturated or unsaturated $C_{11}$-$C_{21}$ alkyl or alkenyl radicals.

Preferably, x and z, which may be identical or different, are 0 or 1.

Advantageously, y is equal to 1.

Preferably, n, g and r, which may be identical or different, are 2 or 3, and even more particularly are equal to 2.

The anion is preferably a halide (chloride, bromide or iodide) or an alkyl sulfate, more particularly methyl sulfate. Use may, however, be made of methanesulfonate, phosphate, nitrate, tosylate, an anion derived from an organic acid such as acetate or lactate, or any other anion compatible with the ammonium containing an ester function.

The anion $X^-$ is even more particularly chloride or methyl sulfate.

Use is more particularly made of the ammonium salts having the formula (VII) in which:

$R_{15}$ denotes a methyl or ethyl radical, x and y are equal to 1;

z is equal to 0 or 1;

n, p and r are equal to 2;

$R_{16}$ is selected from among:

the radical

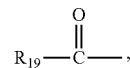

methyl, ethyl or $C_{14}$-$C_{22}$ hydrocarbon-based radicals;

a hydrogen atom;

$R_{18}$ is selected from among:

the radical

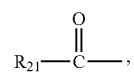

a hydrogen atom;

$R_{17}$, $R_{19}$ and $R_{21}$, which may be identical or different, are selected from among linear or branched, saturated or unsaturated $C_{13}$-$C_{17}$ hydrocarbon-based radicals, and preferably from linear or branched, saturated or unsaturated $C_{13}$-$C_{17}$ alkyl or alkenyl radicals.

Advantageously, the hydrocarbon-based radicals are linear.

Mention may, for example, be made of the compounds having the formula (VII) such as diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate, in particular), and mixtures thereof. The acyl radicals preferably contain 14 to 18 carbon atoms, and originate more particularly from a plant oil such as palm oil or sunflower oil.

When the compound contains several acyl radicals, the latter may be identical or different.

These products are obtained, for example, by direct esterification of triethanolamine, of triisopropanolamine, of alkyldiethanolamine or of alkyldiisopropanolamine, optionally oxyalkylenated, on fatty acids or on mixtures of fatty acids of plant or animal origin, or by transesterification of their methyl esters. This esterification is followed by a quaternization using an alkylating agent such as an alkyl halide (preferably, methyl or ethyl halide), a dialkyl sulfate (preferably, methyl or ethyl sulfate), methyl methanesulfonate, methyl para-toluenesulfonate, glycol chlorohydrin or glycerol chlorohydrin.

Such compounds are, for example, marketed under the trademarks DEHYQUART by HENKEL, STEPANQUAT by STEPAN, NOXAMIUM by CECA and REWOQUAT WE 18 by REWOWITCO.

The compositions according to the invention preferably contain a mixture of quaternary ammonium monoester, diester and triester salts with a majority, by weight, being diester salts.

As a mixture of ammonium salts, use may, for example, be made of the mixture containing 15 to 30% by weight of acyloxyethyldihydroxyethylmethylammonium methyl sulfate, 45 to 60% of diacyloxyethylhydroxyethylmethylammonium methyl sulfate and 15 to 30% of triacyloxyethylmethylammonium methyl sulfate, the acyl radicals having from 14 to 18 carbon atoms and originating from optionally partially hydrogenated palm oil. Use may also be made of the ammonium salts containing at least one ester function described in U.S. Pat. Nos. 4,874,554 and 4,137,180.

Among the quaternary ammonium salts having the formula (IV), preference is given, firstly, to tetraalkylammonium chlorides, for instance dialkyldimethylammonium or alkyltrimethylammonium chlorides, in which the alkyl radical contains approximately from 12 to 22 carbon atoms, in particular behenyltrimethylammonium, distearyldimethylammonium, cetyltrimethylammonium or benzyldimethylstearylammonium chlorides, or else, secondly, the stearamidopropyldimethyl (myristyl acetate) ammonium chloride marketed under the trademark "CERAPHYL 70" by VAN DYK.

According to the invention, behenyltrimethylammonium chloride or behenyltrimethylammonium bromide and CTAB (cetyltrimethylammonium bromine) are the quaternary ammonium salts most particularly preferred.

The fatty amines of the invention correspond to the general formula:

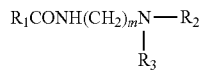

wherein:
R$_1$ is a branched or unbranched, saturated or unsaturated hydrocarbon-based chain containing from 8 and 30 carbon atoms, and preferably from 10 and 24;
R$_2$ and R$_3$ are selected independently from branched or unbranched, saturated or unsaturated hydrocarbons containing from 1 to 10 carbon atoms, and preferably from 1 to 4;
R$_2$ and R$_3$ can also, still independently of one another, correspond to a hydrogen atom H;
M is from 1 to 10, and preferably from 1 to 5.

By way of non-limiting examples, mention will be made of: stearylamine, stearate aminoethylethanolamide, stearyl diethanolamide, stearate diethylenetriamine, stearamidopropyldimethylamine, stearamidopropyldiethylamine, stearamidoethyldiethylamine, stearamidoethyldimethylamine, palmitoamidopropyldimethylamine, palmitoamidopropyldiethylamine, palmitoamidoethyldiethylamine, palmitoamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine and arachidamidoethyldimethylamine.

As a fatty amine which is commercially available, mention may be made of Incromine BB from Croda, Amidoamine MSP from Nikkol, and Lexamine from Inolex.

As other fatty amines, mention will, by way of example, be made of stearylamine, stearate aminoethylethanolamide, stearyl diethanolamide and stearate diethylenetriamine that, inter alia, Sabo sells with the Sabomina series.

Mention will also be made of fatty amine acetates such as the Acetamine series from Kao Corp.

These fatty amines can also be ethoxylated, such as Berol 380, 390, 453 and 455, the Ethomeens from Akzo Nobel or Marlazin L10, OL2, OL20, T15/2, T50 from Condea Chemie.

The particles of the present invention can be introduced into any pharmaceutical carrier for cosmetic, dermatological or ophthalmic purposes. By way of example, mention will be made of lotions, sera, gels and emulsions of all types.

The compositions according to the invention can be in any of the pharmaceutical forms normally used for topical application, for example in the form of solutions, gels, dispersions of the lotion or serum type, emulsions which have a liquid or semi-liquid consistency of the milk type, obtained by dispersion of a fatty phase in an aqueous phase (O/W) or conversely (W/O), or suspensions or emulsions which have a soft, semi-solid or solid consistency of the cream or gel type, or else microemulsions, microcapsules, microparticles or vesicular dispersions of ionic and/or nonionic type. These compositions are prepared according to the usual methods.

The compositions according to the invention can also comprise any additive normally used in the cosmetics or pharmaceutical field.

Of course, those skilled in the art will take care to select this or these optional additional compound(s), and/or the amount thereof, in such manner that the advantageous properties of the composition according to the invention are not, or are not substantially, impaired.

In particular, care will be taken to ensure that this introduction does not harm the stability of the cationic particles associated with the siRNA.

The compositions according to the invention may in particular contain cosmetic or pharmaceutical active agents. This will preferably involve depigmenting agents, sunscreens.

The depigmenting agents which can be incorporated into the composition comprise, for example, the following compounds: kojic acid; ellagic acid; arbutin and derivatives thereof such as those described in EP-895,779 and EP-524,109; hydroquinone; aminophenol derivatives such as those described in WO 99/10318 and WO 99/32077, and in particular N-cholesteryloxycarbonyl-para-aminophenol and N-ethyloxycarbonyl-para-aminophenol; iminophenol derivatives, in particular those described in WO 99/22707; L-2-oxothiazolidine-4-carboxylic acid or procysteine, and its salts and esters; ascorbic acid and its derivatives, in particular ascorbyl glucoside; and plant extracts, in particular extracts of liquorice, mulberry and scullcap, without this list being limiting.

The ultraviolet-radiation-screening agents can be selected from organic UV-screening agents or inorganic UV-radiation-screening agents.

The organic UV-screening agents in accordance with the invention may be water-soluble, liposoluble or insoluble in the usual cosmetic solvents. They are selected in particular from anthranilates; cinnamic derivatives; dibenzoylmethane derivatives; salicylic derivatives, camphor derivatives; triazine derivatives such as those described in U.S. Pat. No. 4,367,390, EP-863,145, EP-517,104, EP-570,838, EP-796,851, EP-775,698, ER-878,469 and EP-933,376; benzophenone derivatives, in particular those described in EP-1-046,391 and DE-10012408; β,β'-diphenyl acrylate derivatives, benzotriazole derivatives, benzimidazole derivatives; imadazolines; bisbenzoazolyl derivatives such as those described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB 2303549, DE 19726184 and EP-893,119; screening polymers and screening silicones such as those described in particular in WO 93/04665; α-alkylstyrene-derived dimers such as those described in DE 19855649; and 4,4-diarylbutadiene derivatives such as those described in EP-0-967,200 and DE 19755649.

The inorganic screening agents are generally pigments or else nanopigments (average size of the primary particles: generally from 5 nm and 100 nm, preferably from 10 nm and 50 nm) of metal oxides which may or may not be coated, such as, for example, nanopigments of titanium oxide (amorphous or crystalline in rutile and/or anatase form), of iron oxide, of zinc oxide, of zirconium oxide or of cerium oxide, which are all UV photoprotective agents well known per se. Conventional coating agents are, moreover, alumina and/or aluminium stearate. Such coated or uncoated metal oxide nanopigments are in particular described in EP-0-518,772 and EP-0-518,773.

The radiation-screening agents in accordance with the invention are generally present in the compositions according to the invention in proportions ranging from 0.1 to 20% by weight relative to the total weight of the composition, and preferably ranging from 0.2 to 15% by weight relative to the total weight of the composition.

The present invention also features the administration of at least one double-stranded RNA oligonucleotide of a sequence selected from the group consisting of SEQ ID NOS. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48 for inhibiting tyrosinase expression.

In particular, the oligonucleotides according to the invention are useful as a bleaching agent and/or as an anti-browning agent for the skin.

The double-stranded RNA oligonucleotides according to the invention can also be used for the formulation of topical, cosmetic or dermatological compositions suited to decrease melanin synthesis, in particular with a view to treating hyperpigmentation, and pigmentation marks and dyschromia, or for bleaching hair follicles, regional hyperpigmentations due to melanocyte hyperactivity, such as idiopathic melasmas, occurring during pregnancy ("pregnancy mask" or chloasma) or oestro-progestin contraception, localized hyperpigmentations due to benign melanocyte hyperactivity and proliferation, such as senile pigmentation marks referred to as actinic lentigo, accidental hyperpigmentations, possibly due to post-lesional wound healing or photosensitization, and also certain forms of leukoderma, such as vitiligo. For the latter (the wound healing possibly resulting in a scar that gives the skin a white appearance), since it is not possible to repigment the lesioned skin, the process is completed by depigmenting the areas of residual normal skin so as to impart to the skin as a whole a homogeneous white tint.

The present invention also features a cosmetic method (regime or regimen) for bleaching and/or lightening the complexion and/or making the color of a browned skin uniform, comprising the topical application of at least one double-stranded RNA oligonucleotide of a sequence selected from the group consisting of SEQ ID NOS. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48.

Preferably, the oligonucleotide is formulated in a topical composition at a concentration of less than or equal to 1 nM.

More preferably, the oligonucleotide is associated with a cationic particle less than or equal to 1 μm in size, with a zeta potential of from 10 to 80 mV, selected from among surfactant micelles, block polymer micelles, liposomes of nonionic and cationic surfactants, niosomes, oleosomes, particles of nanoemulsions, nanocapsules, organic particles or inorganic particles, as described above.

For the purposes of cosmetic, dermatological, ophthalmic or pharmaceutical care, it is sought to avoid invasive methods such as subcutaneous or ocular injections. The cationic particles associated with siRNA according to the present invention can be applied topically to the skin or the mucous membranes or in the eye, in suspension or incorporated into an acceptable cosmocentric carrier, such as lotions, sera, emulsified or non-emulsified gels, oil/water, water/oil or multiple emulsions, microemulsions, etc.

To promote the penetration of the particles associated with siRNA, the water permeability may be modified; thus, it is possible to control the water permeability by measuring the IWL (insensible water loss) with a Tewameter TM210 or a Dermalab—Cortex technology.

By way of example, the following methods may be used:
  stripping (corneodisc, "varnish"), chemical peel or mechanical dermabrasion before application of the compositions according to the invention;
  pretreatment with a mixture of one or more solvents having a defatting effect;
  cleansing the skin with a detergent foaming product;
  occlusive pre- and/or post-treatment either, for example, by covering the surface of the skin to be treated with a watertight synthetic membrane (Blenderm, for example), or by applying a layer of petroleum jelly. This has the effect of blocking the natural IWL of the skin and causing overhydration of the epidermal lipids which thus become more permeable.

After application of the compositions of the present invention, methods may be employed known to those skilled in the art which promote the penetration of molecules into the skin, such as, for example, iontophoresis or electroporation.

In the case of an in vitro skin model, the following treatments may be carried out:
  before deposition of the composition according to the invention, the $Ca^{2+}$ content may be reduced either by changing the medium (0.10-0.75 mM instead of 1.5 mM), or by adding a chelating agent. This has the effect of decreasing intermembrane adhesion, thus increasing the permeability of the skin (Effects of extra- and intracellular calcium concentration on DNA replication, lateral growth, and differentiation of human epidermal cells in culture. Virchows Arch B Cell Pathol Incl Mol. Pathol. 1990; 59(1): 17-25);

using iontophoresis, electroporation and any known methods for modifying the permeability of the model.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Formulations

Cationic Micelles:

Exemplar 1

Octyl-β-glucoside/cetyltriammonium bromide at the molar ratio of 5/1

E1: 100 mM in distilled water
E2: 50 mM in distilled water
E3: 25 mM in distilled water
E4: 12.5 mM in distilled water.

The 2 surfactants (nonionic+cationic) are solubilized in distilled water. A suspension of the siRNA of SEQ ID NO. 1 (20 μM) is added at from 1:1 and 1:9 volume (siRNA:micelles), thus reducing the micellar concentration in proportion.

Exemplar 2

Micelles of decyl-β-glucoside/behenyltriammonium chloride at the molar ratio of 5/1 in distilled water. The same concentrations as in the preceding exemplar are prepared.

These 2 suspensions can be applied to the skin for the treatment of pigmentation marks and dyschromia or for the bleaching of hair follicles.

Cationic Liposomes:

Exemplar 1

"Fluid" Vesicles

| PEG 400 isostearate | 5.5% |
| Behenyltriammonium chloride | 0.5% |
| Distilled water | qs 100 |

Exemplar 2

"Rigid" Vesicles

| Sorbitan palmitate | 2.75% |
| Cholesterol | 2.75% |
| Behenyltriammonium chloride | 0.5% |
| Distilled water | qs 100 |

These examples of liposome suspensions are realized by dialysis. The lipids constituting the vesicles are solubilized in an aqueous solution of octyl-β-glucoside. This solution is then dialyzed against water for 72 h.

The suspension of siRNA SEQ ID NO. 4 is then added, bringing the concentration with respect to the vesicle to around 3% of lipid. This suspension of nonionic liposomes can be applied to the skin for the treatment of pigmentation marks and dyschromia or for the bleaching of hair follicles.

Cationic Oleosomes:

Oil Phase:

| Sucrose mono-distearate marketed by Stéaraineries Dubois | 0.45% |
| Sorbitan stearate 4EO (Tween 61 Uniquema) | 0.30% |
| Behenyltriammonium chloride | 0.21% |
| Vit E acetate | 0.5%: |
| Jojoba oil | 0.5% |
| Stearyl heptanoate | 1% |
| Volatile silicone oil | 1% |
| Vit F glyceride | 0.5% |
| Preservative | 0.02% |
| BHT | 0.01% |

Aqueous Phase:

| Distilled water | qs 100 |
| Preservative | 0.1% |

This dispersion is obtained by high-pressure homogenization in order to have a particle size of approximately 170 nm. A suspension of siRNA SEQ ID NO. 16 (20 μM) at ratios ranging from 1:1 to 1:20 (siRNA/oleosomes) is then added. The siRNA will then complex with the surface of the particles.

Cationic Nanocapsules:

Organic Phase:

| Polycaprolactone (MW: 50 000) | 1% |
| Vit E | 1% |
| Dimethicone copolyol DC2 5695 (Dow Corning) | 0.5% |
| Behenyltriammonium chloride | 0.21% |
| Acetone | 200 ml |

Aqueous Phase:

| Pluronic F68 | 0.5% |
| Distilled water | 200 ml |

The organic phase is introduced with stirring into the aqueous phase. The acetone and 100 ml of aqueous phase are then evaporated off so as to obtain the suspension of nanocapsules, the size of which is 220 nm. A suspension of siRNA SEQ ID NO. 37 (20 μM) at ratios ranging from 1:1 to 1:20 (siRNA/nanocapsules) is then added. The siRNA will then complex with the surface of the particles.

Organic Nanoparticles:

Organic Phase:

| Polyethylene adipate (Scientific Polymer products) | 2% |
| Dimethicone copolyol DC2 5695 (Dow Corning) | 0.5% |
| Behenyltriammonium chloride | 0.21% |
| Acetone | 200 ml |

Aqueous Phase:

| | |
|---|---|
| Pluronic F68 | 0.5% |
| Distilled water | 200 ml |

The organic phase is introduced with stirring into the aqueous phase. The acetone and 100 ml of aqueous phase are then evaporated off so as to obtain the suspension of nanoparticles, the size of which is 180 nm. A suspension of siRNA SEQ ID NO. 40 (20 µM) at ratios ranging from 1:1 to 1:20 (siRNA/nanoparticles) is then added. The siRNA will then complex with the surface of the particles.

Cationic Nanoemulsions:
Oil Phase:

| | |
|---|---|
| PEG 400 isostearate marketed by Uniqema | 1% |
| Behenyltriammonium chloride | 1% |
| Avocado oil | 1% |
| Jojoba oil | 3% |
| Cyclopentamethylsiloxane | 2% |

Aqueous Phase:

| | |
|---|---|
| Distilled water | 30% |
| Dipropylene glycol | 10% |

Dilution Phase:

| | |
|---|---|
| Distilled water | qs 100% |
| Preservative | 0.1% |

An emulsion is prepared by dispersing the oily phase in the aqueous phase with very vigorous stirring. The suspension obtained is then homogenized several times using a very-high-pressure homogenizer, at a pressure of approximately 1200 b. The particle size is of the order of 50 nm and the suspension is transparent. The dilution phase is then added.

As in the previous cases, a suspension of siRNA SEQ ID NO. 42 (20 µM) at ratios ranging from 1:1 to 1:20 (siRNA/nanoemulsion) is then added. The siRNA will then complex with the surface of the particles.

Example 2

Measurement of the Activity of the siRNAs According to the Invention

The effectiveness of the 47 siRNAs of sequence SEQ ID NOS 1 to 47 according to the invention was evaluated in the "pSCREEN-iT™ system" test developed by Invitrogen, set up to evaluate the effectiveness on tyrosinase inhibition (GenBank accession number M27160).

Experimental protocol for the test:
  $2 \times 10^4$ A549 cells/well are seeded into a 48-well plate and cultured overnight.
  Cotransfection is carried out in triplicate for 5 h using 2 µg/ml of Lipofectamine 2000 (Invitrogen) complexed with:
    tyrosinase pScreen-iT™ vector coupled to the LacZ gene—10 ng/well
    luciferase reporter plasmid—20 ng/well
    1 nM Stealth™ RNA The cells are lysed 24 h after the transfection and the β-galactosidase (β-Gal) and luciferase (Luc) activities are measured. The β-Gal/Luc ratio determines the percentage inhibition of tyrosinase.

The results obtained are reported in Table I.

TABLE I

Assaying of the effectiveness of the 47 double-stranded RNA oligonucleotides on the degradation of tyrosinase mRNA (GenBank accession number M27160).

| Oligonucleotide (SEQ ID NO.) | % Inhibition | Oligonucleotide (SEQ ID NO.) | % Inhibition |
|---|---|---|---|
| 1 | 97.50% | 22 | 77.91% |
| 2 | 98.57% | 23 | 97.29% |
| 3 | 86.95% | 24 | 90.50% |
| 4 | 97.95% | 25 | 95.17% |
| 5 | 94.17% | 26 | 90.60% |
| 6 | 77.68% | 27 | 87.11% |
| 7 | 95.86% | 28 | 91.58% |
| 8 | 97.50% | 29 | 96.00% |
| 9 | 87.14% | 30 | 90.39% |
| 10 | 91.54% | 31 | 10.38% |
| 11 | 88.44% | 32 | 97.93% |
| 12 | 89.50% | 33 | 84.79% |
| 13 | 98.15% | 34 | 64.43% |
| 14 | 97.87% | 35 | 97.71% |
| 15 | 36.02% | 36 | 92.12% |
| 16 | 97.78% | 37 | 97.07% |
| 17 | 88.54% | 38 | 9.55% |
| 18 | 81.11% | 39 | 90.22% |
| 19 | 40.78% | 40 | 97.44% |
| 20 | 83.33% | 41 | 88.11% |
| 21 | 92.64% | 42 | 98.71% |
| 43 | 99.10% | 46 | 98.64% |
| 44 | 83.54% | 47 | 94.14% |
| 45 | 89.05% | | |

Secondly, a dose-effect was determined on the 20 sequences which were most effective, i.e., with an effectiveness of greater than 91% at 1 nM. The results are reported in Table II.

TABLE II

Assaying of the effectiveness of the 20 sequences selected, by dose-effect with doses of 0.0016 nM to 1 nM.

| Oligonucleotide (SEQ ID NO.) | 1 nM | 0.25 nM | 0.063 nM | 0.016 nM |
|---|---|---|---|---|
| 1 | 97.37% | 94.34% | 89.47% | 72.07% |
| 2 | 97.98% | 95.64% | 89.34% | 66.68% |
| 4 | 97.93% | 95.22% | 90.24% | 57.92% |
| 5 | 91.33% | 79.88% | 61.47% | 18.40% |
| 7 | 96.86% | 88.97% | 76.45% | 38.34% |
| 8 | 97.84% | 90.76% | 81.12% | 38.57% |
| 13 | 98.13% | 95.73% | 91.11% | 62.56% |
| 14 | 97.59% | 87.22% | 68.77% | 33.87% |
| 16 | 97.95% | 94.92% | 83.40% | 56.25% |
| 23 | 96.05% | 87.42% | 62.32% | 29.97% |
| 25 | 93.45% | 90.50% | 78.36% | 46.80% |
| 29 | 96.42% | 88.24% | 70.64% | 31.15% |
| 32 | 96.88% | 90.69% | 80.33% | 35.04% |
| 35 | 97.42% | 94.84% | 88.34% | 54.29% |
| 37 | 96.38% | 92.46% | 88.24% | 53.92% |
| 40 | 97.65% | 95.08% | 91.59% | 60.64% |
| 42 | 98.25% | 96.54% | 92.58% | 53.46% |
| 43 | 98.46% | 95.60% | 89.21% | 38.85% |
| 46 | 98.77% | 94.81% | 84.23% | 48.74% |
| 47 | 94.60% | 76.71% | 52.94% | 30.18% |

The siRNAs according to the present invention show an effectiveness of greater than 94% at 1 nM for the 20 sequences most effective. The lowest dose tested is 0.016 nM for an effectiveness of 72% on degradation of the mRNA encoding tyrosinase.

Example 3

Evaluation of a Possible Interferon-Type Response Caused by the siRNAs According to the Invention It was verified that the siRNAs which are subjects of the present invention did not induce an interferon-type response. For this, the expression of the OAS-1 and IFIT-1 (interferon-inducible tetratricopeptide repeat domain) genes, known to be induced by interferon (Wieland S F et al., Searching for Interferon-Induced Genes That Inhibit Hepatitis B Virus Replication in Transgenic Mouse Hepatocytes, J. of Virology 2003; 77: 1227-1236. Persengiev S P et al., Nonspecific, concentration-dependent stimulation and repression of mammalian gene expression by small interfering RNAs (siRNAs). RNA 2004; 10: 12-18. Bridge A J et al., Induction of an interferon response by RNAi vectors in mammalian cells. Nature Genet. 2003; 34: 263-264. Scacheri P C et al., Short interfering RNAs can induce unexpected and divergent changes in the levels of untargeted proteins in mammalian cells. Proc. Natl. Acad. Sci. USA 2004, 101: 1892-1897. Sledz C A et al., Activation of the interferon system by short-interfering RNAs. Nat Cell Biol. 2003; 9: 834-9. Patzwahl R et al., Enhanced expression of interferon-regulated genes in the liver of patients with chronic hepatitis C virus infection: detection by suppression-subtractive hybridization. J. Virol. 2001; 75: 1332-1338.), was measured by quantitative PCR (qPCR) according to the protocol described in the "BLOCK-iT™ RNAi Stress Response Control Kit (Human) for monitoring interferon-mediated stress response to double-stranded RNA in human cells" marketed by Invitrogen.

Measurement of the Level of Expression of the hOAS-1 Gene:

The level of expression of the hOAS-1 gene was related to that of the GAPDH reference gene.

| Sample | hOAS-1/GAPDH | Stdev |
| --- | --- | --- |
| dsRNA of SEQ ID NO. 1 - 1 nM | 0.608 | 0.046 |
| dsRNA of SEQ ID NO. 2 - 1 nM | 0.668 | 0.292 |
| dsRNA of SEQ ID NO. 4 - 1 nM | 0.608 | 0.070 |
| dsRNA of SEQ ID NO. 13 - 1 nM | 1.232 | 0.866 |
| dsRNA of SEQ ID NO. 46 - 1 nM | 0.911 | 0.221 |
| dsRNA of SEQ ID NO. 1 - 50 nM | 1.080 | 0.500 |
| Control sequence at 1 nM | 2.141 | 1.336 |
| Positive control (long dsRNA of 1 kb) | 24.905 | 6.431 |
| dsRNA of SEQ ID NO. 1 - 0.1 nM | 0.856 | 0.534 |
| dsRNA of SEQ ID NO. 2 - 0.1 nM | 0.866 | 0.300 |
| dsRNA of SEQ ID NO. 4 - 0.1 nM | 0.966 | 0.568 |
| dsRNA of SEQ ID NO. 13 - 0.1 nM | 1.238 | 0.451 |
| dsRNA of SEQ ID NO. 46 - 0.1 nM | 1.262 | 0.328 |
| Control sequence at 50 nM | 0.807 | 0.404 |
| Control sequence at 0.1 nM | 1.949 | 1.502 |

Result:

Only the positive control (long dsRNA of 1 kb) induces a significant increase in hOAS-1 gene expression. The sequences tested (SEQ ID NOS. 1, 2, 4, 13 and 46) do not significantly increase hOAS-1 gene expression.

Measurement of the Level of Expression of the hIFIT-1 Gene:

| Sample | Threshold cycle | Stdev |
| --- | --- | --- |
| dsRNA of SEQ ID NO. 1 - 1 nM | 36.15 | 0.20 |
| dsRNA of SEQ ID NO. 2 - 1 nM | 32.77 | 1.85 |
| dsRNA of SEQ ID NO. 4 - 1 nM | 35.98 | 0.88 |
| dsRNA of SEQ ID NO. 13 - 1 nM | 35.41 | 1.88 |
| dsRNA of SEQ ID NO. 46 - 1 nM | 34.42 | 3.24 |
| dsRNA of SEQ ID NO. 1 - 50 nM | 34.16 | 3.02 |
| Control sequence at 1 nM | 31.30 | 1.98 |
| Positive control (long dsRNA of 1 kb) | 25.70 | 0.79 |
| dsRNA of SEQ ID NO. 1 - 0.1 nM | 32.47 | 3.07 |
| dsRNA of SEQ ID NO. 2 - 0.1 nM | 35.38 | 1.41 |
| dsRNA of SEQ ID NO. 4 - 0.1 nM | 34.86 | 1.86 |
| dsRNA of SEQ ID NO. 13 - 0.1 nM | 33.22 | 2.33 |
| dsRNA of SEQ ID NO. 46 - 0.1 nM | 33.89 | 2.03 |
| Control sequence at 50 nM | 35.70 | 3.30 |
| Control sequence at 0.1 nM | 33.65 | 3.90 |

Result:

Only the positive control (long dsRNA of 1 kb) induces a significant expression of the hIFIT-1 gene detected at a threshold cycle value of approximately 25. The sequences tested (SEQ ID NOS. 1, 2, 4, 13 and 46) induce hIFIT-1 gene expression only for threshold cycle values of approximately 32-36, i.e., a difference of 7-11 cycles corresponding to an amount of messengers which is $10^2$-$10^3$ times lower.

These assays make it possible to conclude that the dsRNAs according to the invention do not induce an interferon-type response.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for inhibiting tyrosinase expression in a subject, wherein said method comprises administering an effective amount of at least one double-stranded RNA oligonucleotide having a sense strand consisting of a sequence selected from the group consisting of SEQ ID NOs 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47 and a complementary anti-sense strand to said subject.

2. The method according to claim 1, further comprising co-administering a population of cationic particulates less than or equal to 1 μm in size having a zeta potential ranging from 10 to 80 mV, wherein said population of cationic particulates comprises surfactant micelles, liposomes of non-ionic and cationic surfactants, niosomes, oleosomes, particles of nanoemulsions, nanocapsules, organic particles, or inorganic particles, and wherein said double-stranded oligonucleotide has blunt ends.

3. The method according to claim 1 or claim 2, wherein said sequence is selected from the group consisting of SEQ ID NOs 1, 2, 4, 5, 7, 8, 13, 14, 16, 23, 25, 29, 32, 35, 37, 40, 42 43, 46, and 47.

4. The method according to claim 1 or claim 2, wherein said sequence is selected from the group consisting of SEQ ID NOs 1, 2, 4, 13, 16, 35, 37, 40, and 42 and wherein said double-stranded RNA oligonucleotide has a tyrosinase mRNA degradation efficiency of greater than 50% at 0.016 nM when evaluated.

5. The method according to claim 1 or claim 2, wherein said administration is topical administration.

* * * * *

SEQUENCE LISTING

<160> NUMBER OF SEQ ID NOS: 48

<210> SEQ ID NO 1
<211> LENGTH: 25
<212> TYPE: RNA
<213> ORGANISM: Homo sapiens

<400> SEQUENCE: 1
gcguaauccu ggaaaccaug acaaa                                              25

<210> SEQ ID NO 2
<211> LENGTH: 25
<212> TYPE: RNA
<213> ORGANISM: Homo sapiens

<400> SEQUENCE: 2
gccuaccuca cuuuagcaaa gcaua                                              25

<210> SEQ ID NO 3
<211> LENGTH: 25
<212> TYPE: RNA
<213> ORGANISM: Homo sapiens

<400> SEQUENCE: 3
ccugugucuc cucuaagaac cugau                                              25

<210> SEQ ID NO 4
<211> LENGTH: 25
<212> TYPE: RNA
<213> ORGANISM: Homo sapiens

<400> SEQUENCE: 4 ccaugggac cuauggccaa augaa                                               25

<210> SEQ ID NO 5
<211> LENGTH: 25
<212> TYPE: RNA
<213> ORGANISM: Homo sapiens

<400> SEQUENCE: 5
ccgauuggag gaguacaaca gccau                                              25

<210> SEQ ID NO 6
<211> LENGTH: 25
<212> TYPE: RNA
<213> ORGANISM: Homo sapiens

<400> SEQUENCE: 6
ggaccuuuac ggcguaaucc uggaa                                              25

<210> SEQ ID NO 7
<211> LENGTH: 25
<212> TYPE: RNA
<213> ORGANISM: Homo sapiens

<400> SEQUENCE: 7
ggcguaaucc uggaaaccau gacaa                                              25

<210> SEQ ID NO 8
<211> LENGTH: 25
<212> TYPE: RNA
<213> ORGANISM: Homo sapiens

<400> SEQUENCE: 8
ccugucagaa uauccuucug uccaa                                              25

<210> SEQ ID NO 9
<211> LENGTH: 25
<212> TYPE: RNA
<213> ORGANISM: Homo sapiens

<400> SEQUENCE: 9

```
ccuggaaacc augacaaauc cagaa                                              25

<210> SEQ ID NO 10
<211> LENGTH: 25
<212> TYPE: RNA
<213> ORGANISM: Homo sapiens

<400> SEQUENCE: 10
ccaauaugaa ucugguucca uggau                                              25

<210> SEQ ID NO 11
<211> LENGTH: 25
<212> TYPE: RNA
<213> ORGANISM: Homo sapiens

<400> SEQUENCE: 11
gguuccaugg auaaagcugc caauu                                              25

<210> SEQ ID NO 12
<211> LENGTH: 25
<212> TYPE: RNA
<213> ORGANISM: Homo sapiens

<400> SEQUENCE: 12
gcaaagcaua ccaucagcuc agacu                                              25

<210> SEQ ID NO 13
<211> LENGTH: 25
<212> TYPE: RNA
<213> ORGANISM: Homo sapiens

<400> SEQUENCE: 13
ggaguacaac agccaucagu cuuua                                              25

<210> SEQ ID NO 14
<211> LENGTH: 25
<212> TYPE: RNA
<213> ORGANISM: Homo sapiens

<400> SEQUENCE: 14
gcagagguuc cugucagaau auccu                                              25

<210> SEQ ID NO 15
<211> LENGTH: 25
<212> TYPE: RNA
<213> ORGANISM: Homo sapiens

<400> SEQUENCE: 15
gcagauuguc uguagccgau uggag                                              25

<210> SEQ ID NO 16
<211> LENGTH: 25
<212> TYPE: RNA
<213> ORGANISM: Homo sapiens

<400> SEQUENCE: 16
gaucaacacc cauguuuaac gacau                                              25

<210> SEQ ID NO 17
<211> LENGTH: 25
<212> TYPE: RNA
<213> ORGANISM: Homo sapiens
```

```
<400> SEQUENCE: 17
gaguacaaca gccaucaguc uuuau                                          25

<210> SEQ ID NO 18
<211> LENGTH: 25
<212> TYPE: RNA
<213> ORGANISM: Homo sapiens

<400> SEQUENCE: 18
gcauuauuau gugucaaugg augca                                          25

<210> SEQ ID NO 19
<211> LENGTH: 25
<212> TYPE: RNA
<213> ORGANISM: Homo sapiens

<400> SEQUENCE: 19
gaccuuuacg gcguaauccu ggaaa                                          25

<210> SEQ ID NO 20
<211> LENGTH: 25
<212> TYPE: RNA
<213> ORGANISM: Homo sapiens

<400> SEQUENCE: 20
gccuuggcau agacucuucu uguug                                          25

<210> SEQ ID NO 21
<211> LENGTH: 25
<212> TYPE: RNA
<213> ORGANISM: Homo sapiens

<400> SEQUENCE: 21
gcacagauga guacauggga gguca                                          25

<210> SEQ ID NO 22
<211> LENGTH: 25
<212> TYPE: RNA
<213> ORGANISM: Homo sapiens

<400> SEQUENCE: 22
gagagacgac ucuuggugag aagaa                                          25

<210> SEQ ID NO 23
<211> LENGTH: 25
<212> TYPE: RNA
<213> ORGANISM: Homo sapiens

<400> SEQUENCE: 23
gaggaguaca acagccauca gucuu                                          25

<210> SEQ ID NO 24
<211> LENGTH: 25
<212> TYPE: RNA
<213> ORGANISM: Homo sapiens

<400> SEQUENCE: 24
ucuguagccg auuggaggag uacaa                                          25

<210> SEQ ID NO 25
<211> LENGTH: 25
<212> TYPE: RNA
<213> ORGANISM: Homo sapiens
```

```
<400> SEQUENCE: 25
ucccuagagc cugugucucc ucuaa                                              25

<210> SEQ ID NO 26
<211> LENGTH: 25
<212> TYPE: RNA
<213> ORGANISM: Homo sapiens

<400> SEQUENCE: 26
ucuuggcaga uugucuguag ccgau                                              25

<210> SEQ ID NO 27
<211> LENGTH: 25
<212> TYPE: RNA
<213> ORGANISM: Homo sapiens

<400> SEQUENCE: 27
ucuuguugcg gugggaacaa gaaau                                              25

<210> SEQ ID NO 28
<211> LENGTH: 25
<212> TYPE: RNA
<213> ORGANISM: Homo sapiens

<400> SEQUENCE: 28
gccaucaguc uuuaugcaau ggaac                                              25

<210> SEQ ID NO 29
<211> LENGTH: 25
<212> TYPE: RNA
<213> ORGANISM: Homo sapiens

<400> SEQUENCE: 29
ccaaacugca cagagagacg acucu                                              25

<210> SEQ ID NO 30
<211> LENGTH: 25
<212> TYPE: RNA
<213> ORGANISM: Homo sapiens

<400> SEQUENCE: 30
ccugaguuug acccaauaug aaucu                                              25

<210> SEQ ID NO 31
<211> LENGTH: 25
<212> TYPE: RNA
<213> ORGANISM: Homo sapiens

<400> SEQUENCE: 31
ccaauuagcc aguccugca gaccu                                               25

<210> SEQ ID NO 32
<211> LENGTH: 25
<212> TYPE: RNA
<213> ORGANISM: Homo sapiens

<400> SEQUENCE: 32
ggaggaguac aacagccauc agucu                                              25

<210> SEQ ID NO 33
<211> LENGTH: 25
<212> TYPE: RNA
```

<213> ORGANISM: Homo sapiens

<400> SEQUENCE: 33
ccauggauaa agcugccaau uucag                                         25

<210> SEQ ID NO 34
<211> LENGTH: 25
<212> TYPE: RNA
<213> ORGANISM: Homo sapiens

<400> SEQUENCE: 34
acucuucuug uugcgguggg aacaa                                         25

<210> SEQ ID NO 35
<211> LENGTH: 25
<212> TYPE: RNA
<213> ORGANISM: Homo sapiens

<400> SEQUENCE: 35
acaacagcca ucagucuuua ugcaa                                         25

<210> SEQ ID NO 36
<211> LENGTH: 25
<212> TYPE: RNA
<213> ORGANISM: Homo sapiens

<400> SEQUENCE: 36
accucacuuu agcaaagcau accau                                         25

<210> SEQ ID NO 37
<211> LENGTH: 25
<212> TYPE: RNA
<213> ORGANISM: Homo sapiens

<400> SEQUENCE: 37
gucuggaugc auuauuaugu gucaa                                         25

<210> SEQ ID NO 38
<211> LENGTH: 25
<212> TYPE: RNA
<213> ORGANISM: Homo sapiens

<400> SEQUENCE: 38
accuugugag gacuagagga agaau                                         25

<210> SEQ ID NO 39
<211> LENGTH: 25
<212> TYPE: RNA
<213> ORGANISM: Homo sapiens

<400> SEQUENCE: 39
guuccaugga uaaagcugcc aauuu                                         25

<210> SEQ ID NO 40
<211> LENGTH: 25
<212> TYPE: RNA
<213> ORGANISM: Homo sapiens

<400> SEQUENCE: 40
acagagagac gacucuuggu gagaa                                         25

<210> SEQ ID NO 41
<211> LENGTH: 25

```
<212> TYPE: RNA
<213> ORGANISM: Homo sapiens

<400> SEQUENCE: 41
gccugugucu ccucuaagaa ccuga                                    25

<210> SEQ ID NO 42
<211> LENGTH: 25
<212> TYPE: RNA
<213> ORGANISM: Homo sapiens

<400> SEQUENCE: 42
ucaggcagag guuccuguca gaaua                                    25

<210> SEQ ID NO 43
<211> LENGTH: 25
<212> TYPE: RNA
<213> ORGANISM: Homo sapiens

<400> SEQUENCE: 43
caacagccau cagucuuuau gcaau                                    25

<210> SEQ ID NO 44
<211> LENGTH: 25
<212> TYPE: RNA
<213> ORGANISM: Homo sapiens

<400> SEQUENCE: 44
gcauaccauc agcucagacu auguc                                    25

<210> SEQ ID NO 45
<211> LENGTH: 25
<212> TYPE: RNA
<213> ORGANISM: Homo sapiens

<400> SEQUENCE: 45
ccaucagucu uuaugcaaug gaacg                                    25

<210> SEQ ID NO 46
<211> LENGTH: 25
<212> TYPE: RNA
<213> ORGANISM: Homo sapiens

<400> SEQUENCE: 46
ggaucaacac ccauguuuaa cgaca                                    25

<210> SEQ ID NO 47
<211> LENGTH: 25
<212> TYPE: RNA
<213> ORGANISM: Homo sapiens

<400> SEQUENCE: 47
cagagguucc ugucagaaua uccuu                                    25

<210> SEQ ID NO 48
<211> LENGTH: 19
<212> TYPE: RNA
<213> ORGANISM: Homo sapiens

<400> SEQUENCE: 48
ugcaccacuu gggccucaa                                           19
```